(12) United States Patent
Jimenez et al.

(10) Patent No.: US 11,745,183 B2
(45) Date of Patent: Sep. 5, 2023

(54) MICROTITER PLATE AND USES THEREOF

(71) Applicant: ONEXIO BIOSYSTEMS LLC, Madison, WI (US)

(72) Inventors: Jose Jimenez, Madison, WI (US); Brian Johnson, Madison, WI (US); David Beebe, Monona, WI (US)

(73) Assignee: ONEXIO BIOSYSTEMS LLC, Madison, WI (US)

( * ) Notice: Subject to any disclaimer, the term of this patent is extended or adjusted under 35 U.S.C. 154(b) by 301 days.

(21) Appl. No.: 16/694,096

(22) Filed: Nov. 25, 2019

(65) Prior Publication Data
US 2020/0086311 A1 Mar. 19, 2020

Related U.S. Application Data

(63) Continuation of application No. 16/168,476, filed on Oct. 23, 2018, now Pat. No. 10,518,266, which is a
(Continued)

(51) Int. Cl.
*B01L 3/00* (2006.01)
*C12M 1/32* (2006.01)
(Continued)

(52) U.S. Cl.
CPC ............. *B01L 3/5085* (2013.01); *C12M 1/18* (2013.01); *C12M 23/12* (2013.01); *C12M 23/16* (2013.01);
(Continued)

(58) Field of Classification Search
CPC .......... B01L 3/5082; B01L 2300/0681; B01L 2300/069; B01L 2300/0829; B01L 2300/0851; C12M 1/18; C12M 23/12; C12M 23/16; C12M 23/24; C12M 23/34; C12M 25/04; C12M 29/04
See application file for complete search history.

(56) References Cited

U.S. PATENT DOCUMENTS 9,573,128 B1   2/2017  McClelland
10,518,266 B2  12/2019 Johnson et al.
(Continued)

FOREIGN PATENT DOCUMENTS

EP          3032257 A1      6/2016
WO     WO 2009/148509 A1   12/2009
(Continued)

OTHER PUBLICATIONS

International Search Report of related PCT/US2017/041204, dated Sep. 29, 2017, 12 pages.
(Continued)

*Primary Examiner* — Michael L Hobbs
(74) *Attorney, Agent, or Firm* — CASIMIR JONES, S.C.; DAIVD A. CASIMIR; TANYA A. ARENSON

(57) ABSTRACT

Provided herein are microtiter plates, systems, and uses thereof. In particular, provided herein are cell culture (e.g., microtiter plates) with a plurality of wells that comprise
(Continued)

diffusion channels, systems comprising the devices (e.g., comprising cells), and use of the devices and systems in co-culture applications (e.g. in high throughput screening) and biological assays.

16 Claims, 15 Drawing Sheets

Related U.S. Application Data continuation of application No. PCT/US2017/041204, filed on Jul. 7, 2017.

(60) Provisional application No. 62/359,977, filed on Jul. 8, 2016, provisional application No. 62/359,483, filed on Jul. 7, 2016.

(51) Int. Cl.
  *C12M 1/00* (2006.01)
  *C12M 1/18* (2006.01)
  *C12M 3/06* (2006.01)
  *C12M 1/04* (2006.01)
  *C12M 1/12* (2006.01)

(52) U.S. Cl.
  CPC ............ *C12M 23/24* (2013.01); *C12M 23/34* (2013.01); *C12M 25/04* (2013.01); *C12M 29/04* (2013.01); *B01L 2300/069* (2013.01); *B01L 2300/0681* (2013.01); *B01L 2300/0829* (2013.01); *B01L 2300/0851* (2013.01)

(56) References Cited

U.S. PATENT DOCUMENTS

| | | | |
|---|---|---|---|
| 2004/0002131 A1* | 1/2004 | Kim | B01L 3/5025 435/33 |
| 2009/0298116 A1* | 12/2009 | Fang | B01L 3/5085 430/320 |
| 2011/0217725 A1 | 9/2011 | Itchoda et al. | |
| 2015/0004686 A1* | 1/2015 | Goral | C12M 35/08 435/305.1 |
| 2015/0093306 A1 | 4/2015 | Thorne et al. | |
| 2016/0114322 A1 | 4/2016 | Ismagilov et al. | |
| 2016/0334388 A1* | 11/2016 | McClelland | B01L 3/502715 |
| 2016/0348148 A1 | 12/2016 | Wu et al. | |
| 2017/0227525 A1* | 8/2017 | Griffith | F04B 43/043 |

FOREIGN PATENT DOCUMENTS

| | | |
|---|---|---|
| WO | WO 2015/051678 A1 | 4/2015 |
| WO | WO 2018/009870 | 1/2018 |

OTHER PUBLICATIONS

Goers et al., "Co-culture systems and technologies: taking synthetic biology to the next level." J R Soc Interface. Jul. 6, 2014;11(96).

Goral et al., "A continuous perfusion microplate for cell culture." Lab Chip. Mar. 21, 2013;13(6):1039-43.

Wilming, A. et al. Fed-batch operation in special microtiter plates: a new method for screening under production conditions. J Ind Microbiol Biotechnol. Mar. 2014;41(3):513-25.

* cited by examiner

FIG. 3
Fig. 3A
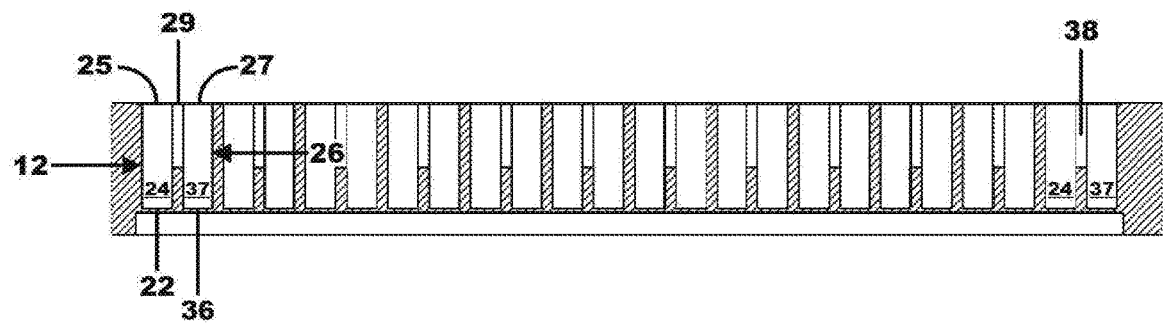
Fig. 3B
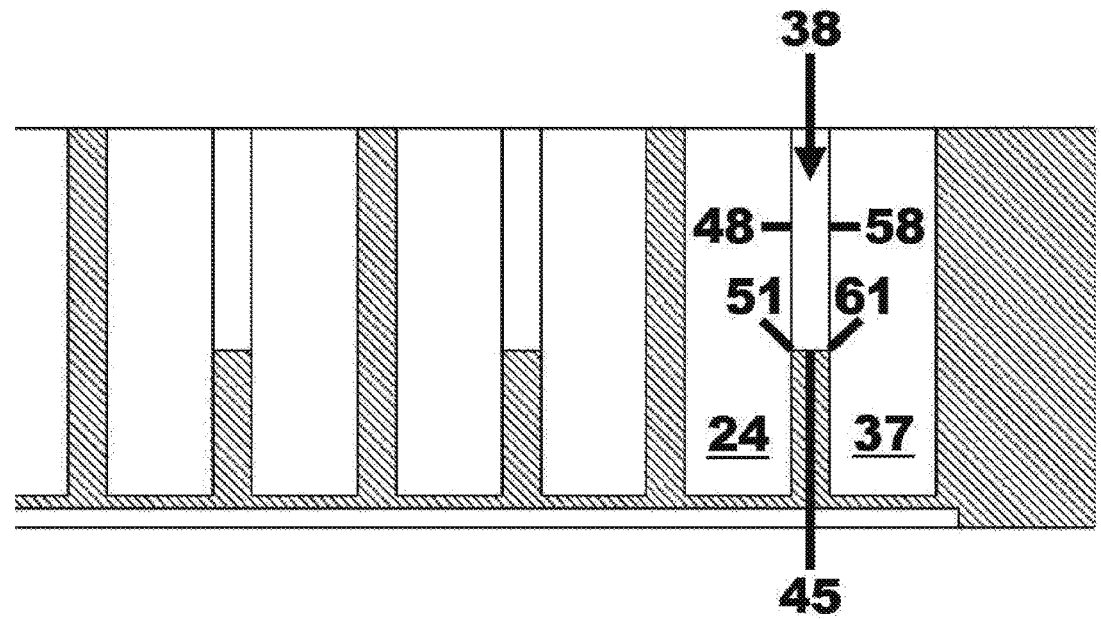

FIG. 4
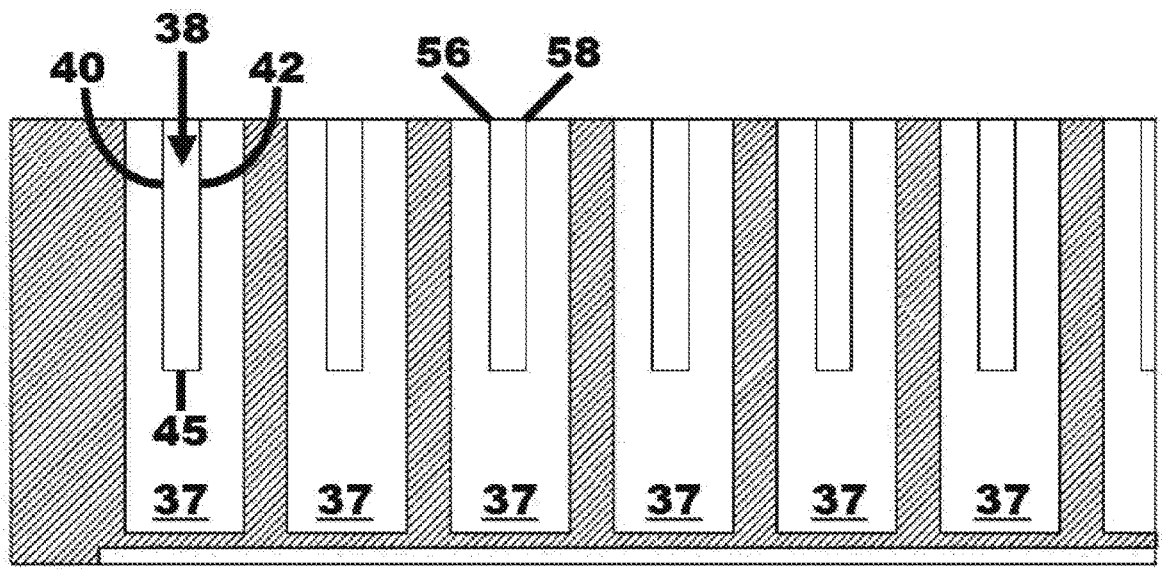
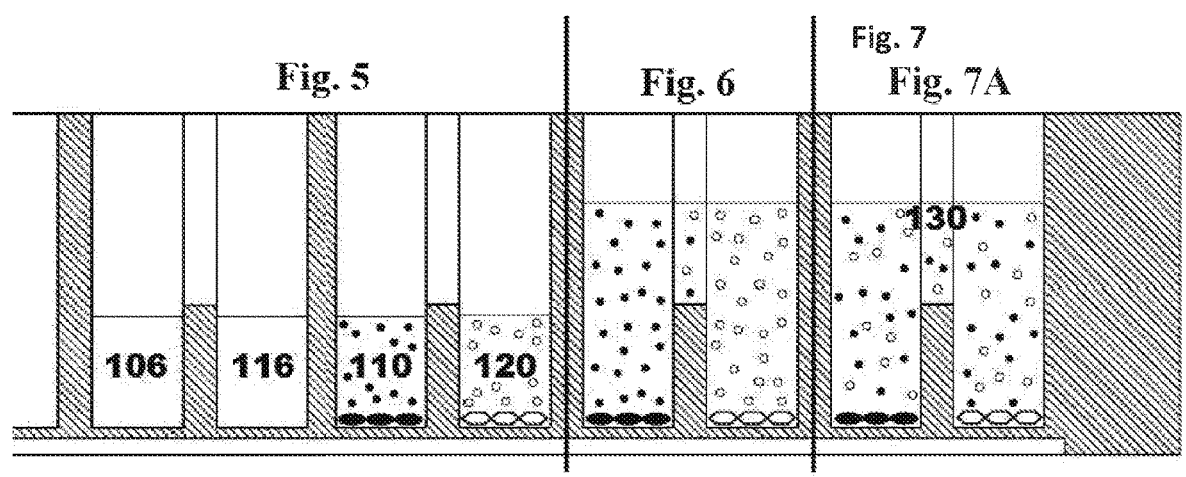
FIG. 7B
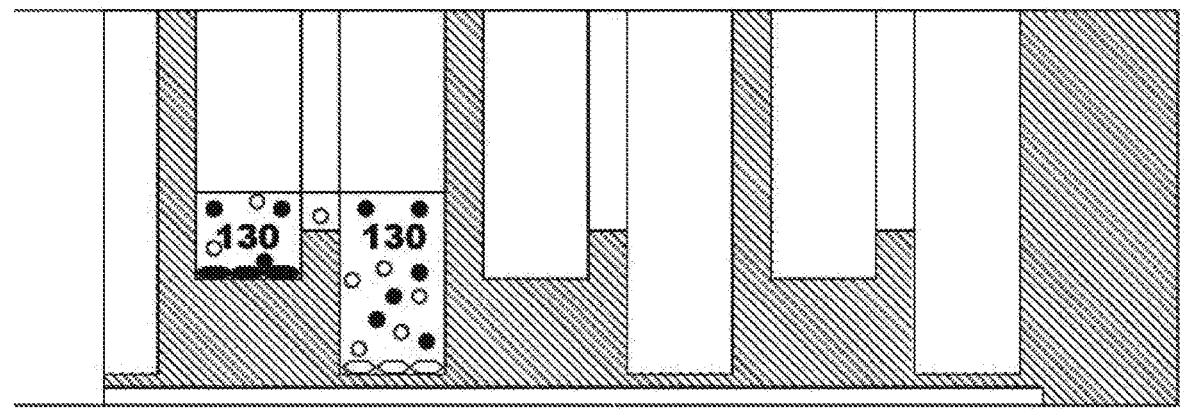

FIG. 17
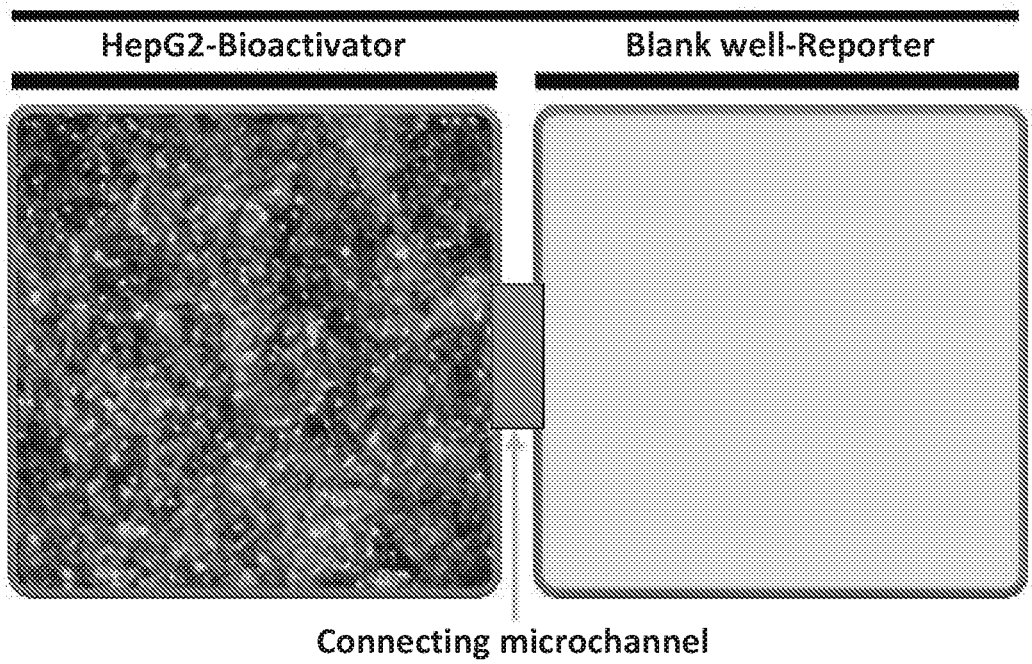
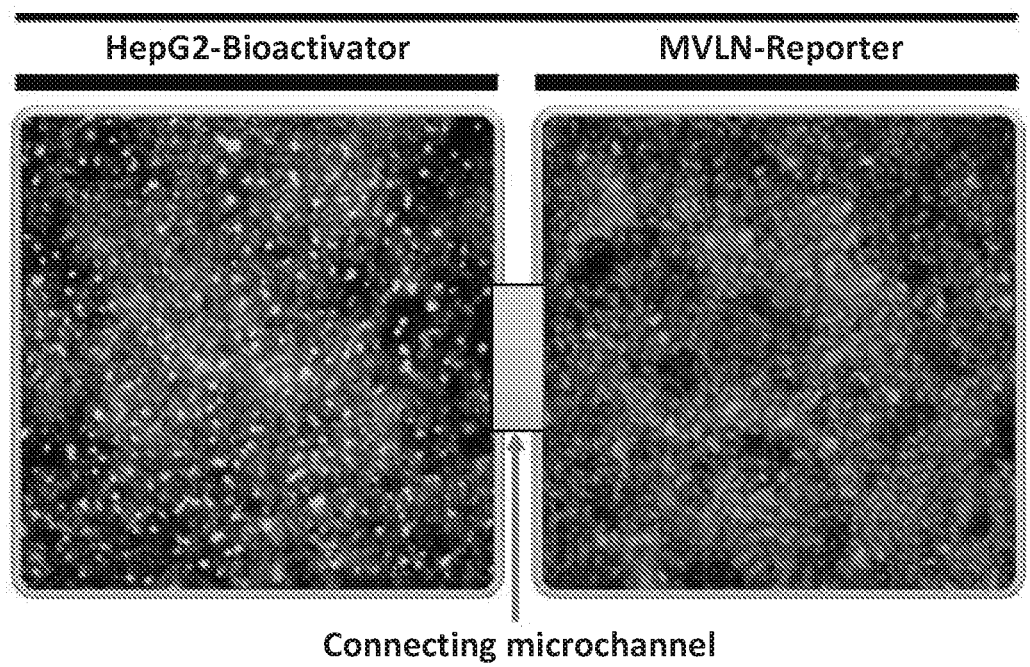

MICROTITER PLATE AND USES THEREOF

FIELD OF DISCLOSURE

Provided herein are microtiter plates, systems, and uses thereof. In particular, provided herein are microtiter plates with diffusion channels and their use in co-culture applications (e.g. in high throughput screening).

BACKGROUND

Current high throughput screening (HTS) assays typically only include one cell type with limited metabolic competence. Therefore, drugs and chemicals that are naturally metabolized by liver hepatocytes or other cell types into active compounds or become quickly detoxified generate false-negative and false-positive results, respectively. Existing co-culture or multi-culture devices are expensive and are poorly suited to higher density 96, 384 and 1536 well microtiter plates. A simple co-culture platform would greatly improve the accuracy of the HTS assays.

SUMMARY

Provided herein are microtiter plates, systems, and uses thereof In particular, provided herein are microtiter plates with diffusion channels and their use in co-culture applications (e.g. in high throughput screening).

For example, in some embodiments, provided herein is a cell culture device, comprising: an upper surface and a lower surface, wherein the lower surface comprises a plurality of wells, wherein at least a portion of the wells comprise a diffusion channel (e.g., micro channel) between a first well and an adjacent well, and wherein the well further comprises a first end wall and a second end wall. In some embodiments, the channel comprises adjacent end walls that are lower in height than said well. In some embodiments, the adjacent end walls are parallel. In some embodiments, in at least a portion of said wells, the first end wall is higher than the second end wall. In some embodiments, in each of the wells, the first end wall is higher than the second end wall. In some embodiments, each well comprises a first end wall adjacent to the first end wall of the adjacent well and a second end wall adjacent to the second end wall of the adjacent well. In some embodiments, the device is a microtiter plate (e.g., comprising 6, 24, 96, 384 or 1536 wells). In some embodiments, the channels are filled with a membrane (e.g., gel, hydrogel, porous membrane, etc.). In some embodiments, the membrane allows for size exclusion and/or diffusion control of metabolites or proteins that pass between wells.

Further embodiments provide a kit or system, comprising: any of the devices described herein; and a plurality of cells. In some embodiments, the kit or system further comprises one or more additional components selected from, for example, a fluid, a fluid transport component, a plurality of second cells of a different cell type, a test compound, or components for performing a biological assay. The present disclosure is not limited to particular cell types. Examples include, but are not limited to, primary cells, immortalized cells, microbial cells, or pluripotent (e.g., stem) cells. In some embodiments, the second cells are reporter cells. In some embodiments, the fluid is buffer or culture media. In some embodiments, the biological assay is, for example, a gene expression assay, a cell signaling assay, a toxicity assay, or a drug screening assay.

Certain embodiments provide a reaction mixture comprising a device described herein comprising a first cell in a first well and a second cell type or assay in an adjacent well.

Additional embodiments provide a cell culture method, comprising: a) contacting the device, kit or system described herein with one or more cells; and b) culturing the cells. In some embodiments, the method further comprises contacting the kit or system with second cells or biological assay reagents. In some embodiments, the cells and second cells are in adjacent wells of the device. In some embodiments, the method further comprises the step of contacting the device with media or buffer such that adjacent cells are in fluid contact. In some embodiments, metabolites or proteins secreted from the cells travel through the channels to wells comprising the second cells or biological assay. In some embodiments, the method further comprises the step of performing a biological assay on wells comprising the second cells or biological assay reagents. In some embodiments, the method is a high throughput assay.

Yet other embodiments provide a method of performing an assay, comprising: a) contacting the devices described herein with a plurality of cells assay reagents (e.g., comprising a second cell type), wherein the cells and biological assay reagents are in adjacent wells; b) adding media or buffer to the device such that adjacent cells are in fluid contact; and c) performing a biological assay on the wells comprising the biological assay reagents. In some embodiments, the biological assay reagents include reagents for performing an assay selected from the group consisting of a sequencing assay, an amplification assay, an immunoassay, an enzyme assay, etc. In some embodiments, assay results are detected via fluorescence, luminescence, etc.

Additional embodiments are described herein.

DESCRIPTION OF FIGURES

FIG. 3: FIG. 3A is a schematic, cross-sectional view of adevice of embodiments of the present disclosure taken along line 3-3 of FIG. 2. FIG. 3B is a close-up view thereof.

FIG. 4 is a schematic, cross-sectional view of adevice of embodiments of the present disclosure taken 6 wells along line 4-4 of FIG. 2.

FIG. 5 is a schematic, cross-sectional view of a device of embodiments of the present disclosure, similar to FIG. 3, showing an initial step of the methodology of the present disclosure; FIG. 3 but with low media.

FIG. 6 is a schematic, cross-sectional view of a device of embodiments of the present disclosure, similar to FIG. 3, showing a second step of the methodology of the present disclosure; FIG. 3 with high media and metabolites undiffused.

FIG. 7: FIG. 7A is a schematic, cross-sectional view of adevice of embodiments of the present disclosure, described. FIG. 7B is a schematic, cross-sectional view of a device of embodiments of the present disclosure similar to FIG. 7A showing differential well heights.

FIG. 17 shows that HepG2 and MVLN cells are viable and healthy after 5 days of culture in exemplary microtiter plates described herein.

FIG. 18A) and FIG. 18B) Cytotoxicity screens show that HEK293 cells in the device (grey squares) have increased sensitivity compared to mono-culture (black squares), and that the response depends on the cell type used for metabolism. Bioactivator toxicity can also be measured real time (triangles). FIG. 18C) ER-transactivation in MVLNs shows competence in 4-benzylphenol but not in methoxychlor.

DEFINITIONS

Figures 1, 1A:
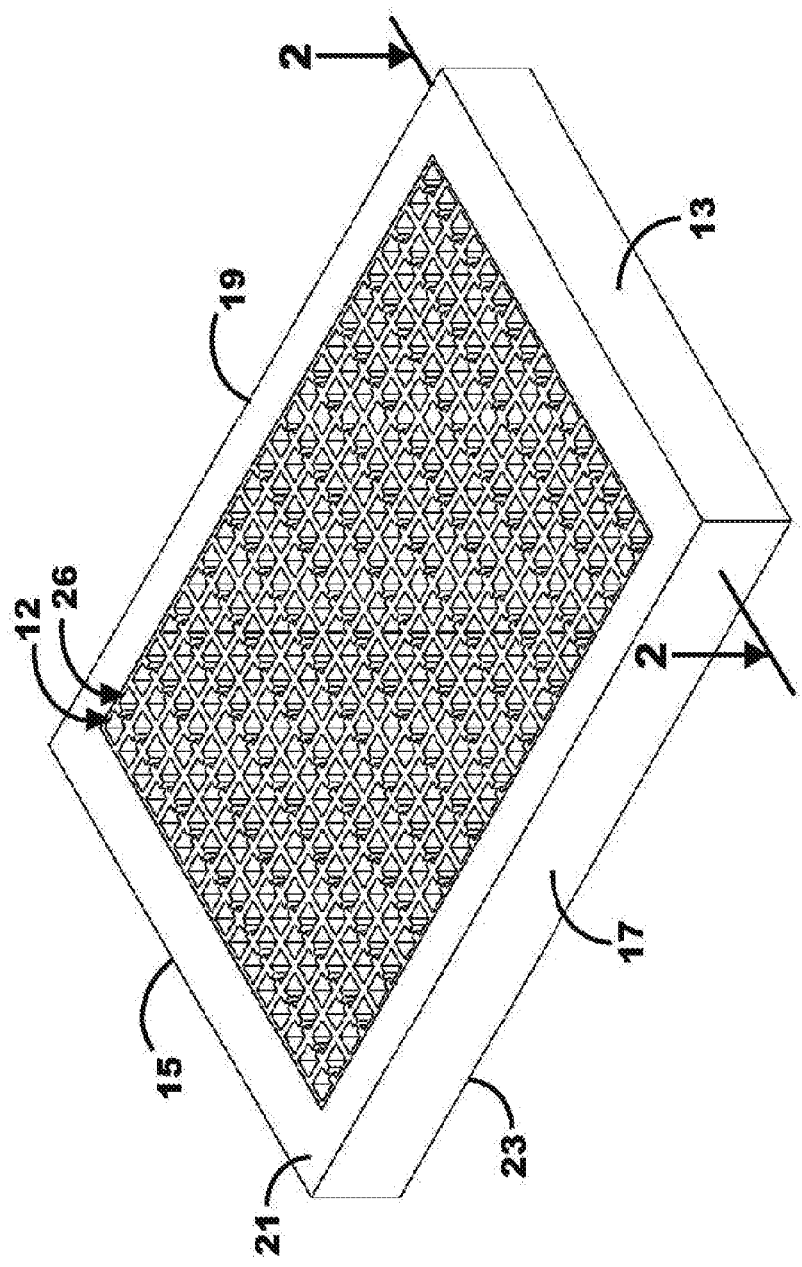
FIG. 1.
FIG. 1A is an isometric view of a device (Device 10) of embodiments of the present disclosure in an initial configuration.
Figures 1, 1B:
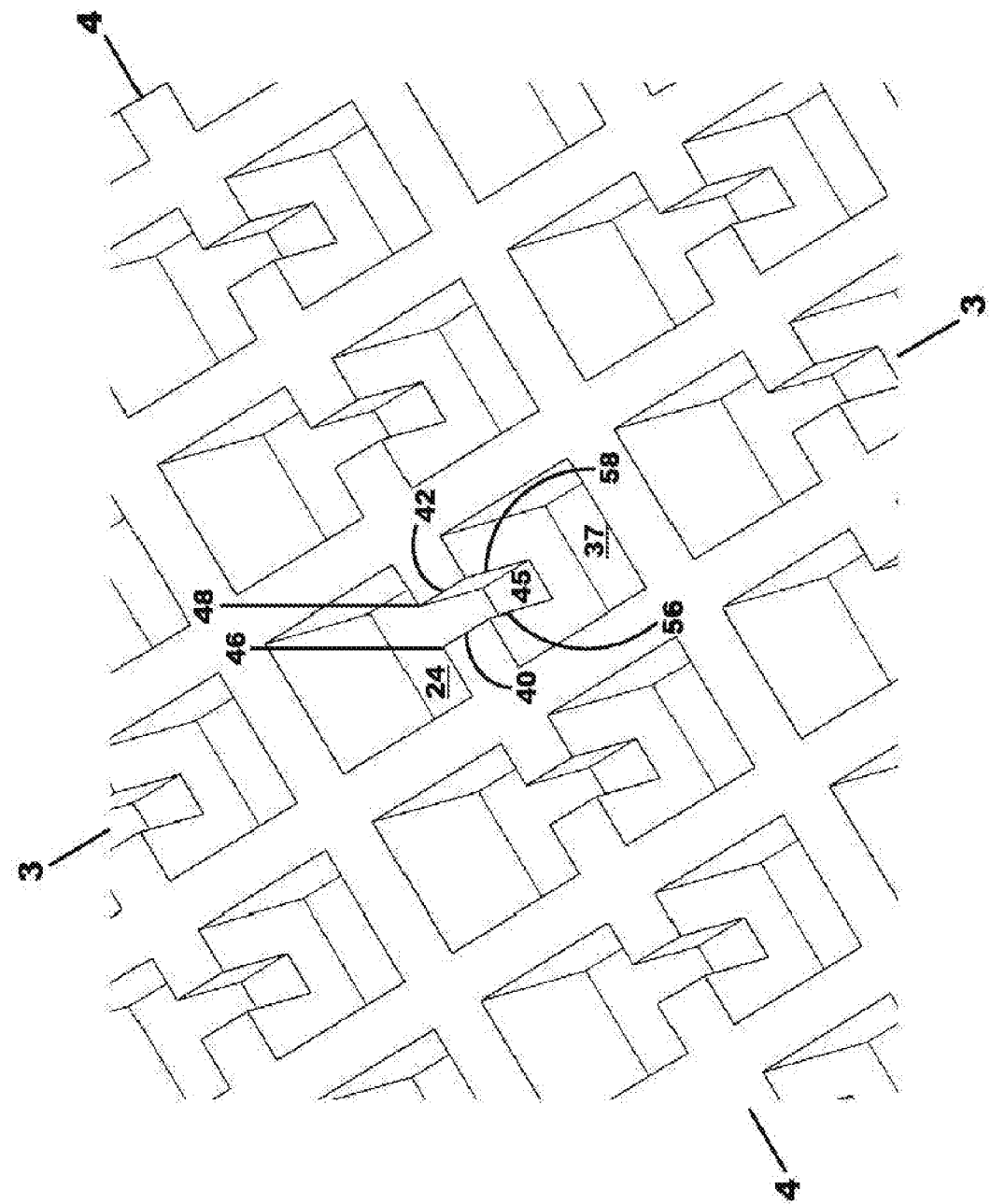
FIG. 1B is a close up view thereof.
Figures 2, 2A:
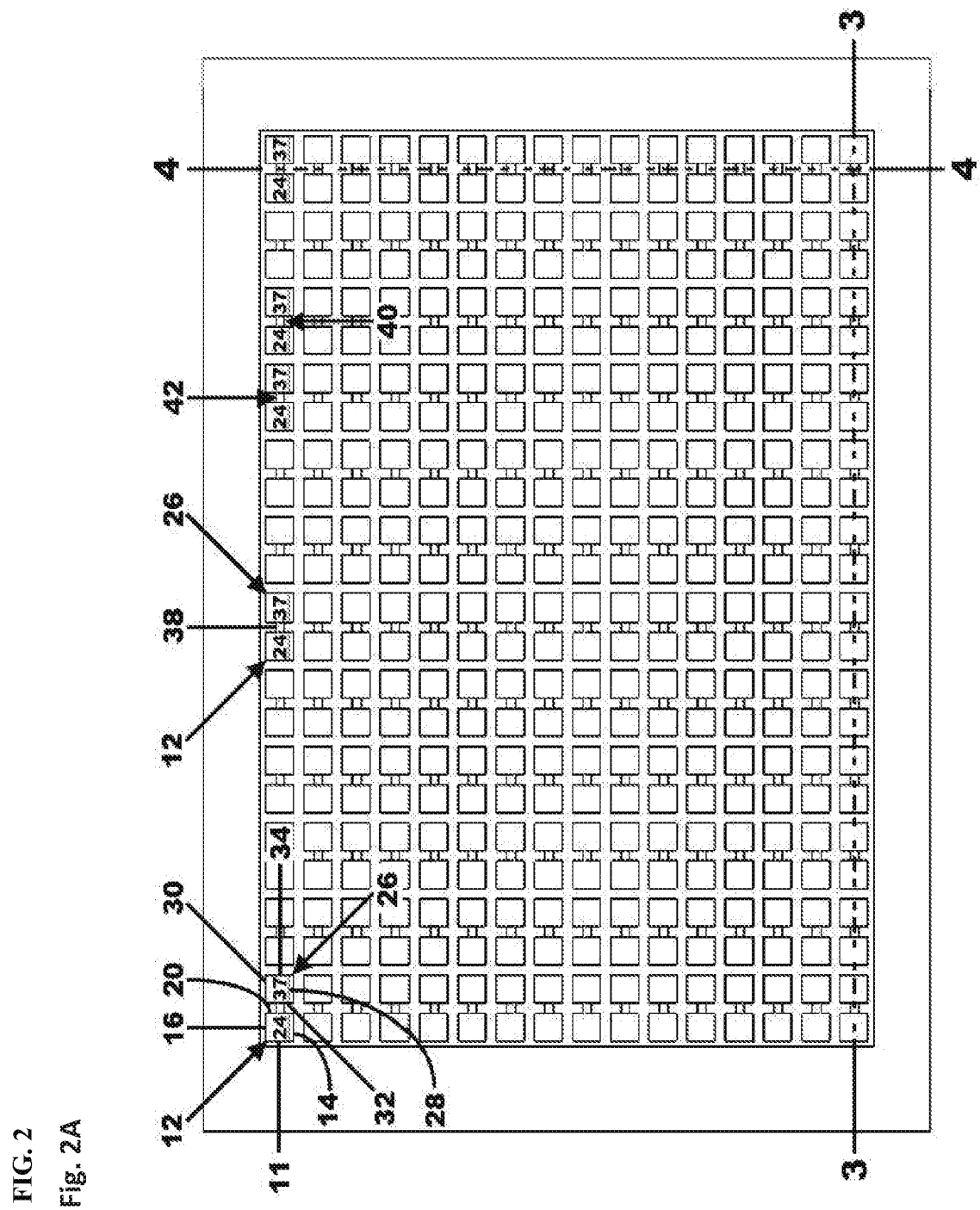
FIG. 2.
FIG. 2A is a schematic, top view of a device of embodiments of the present disclosure taken along line 2-2 of FIG. 1.
Figures 2, 2B:
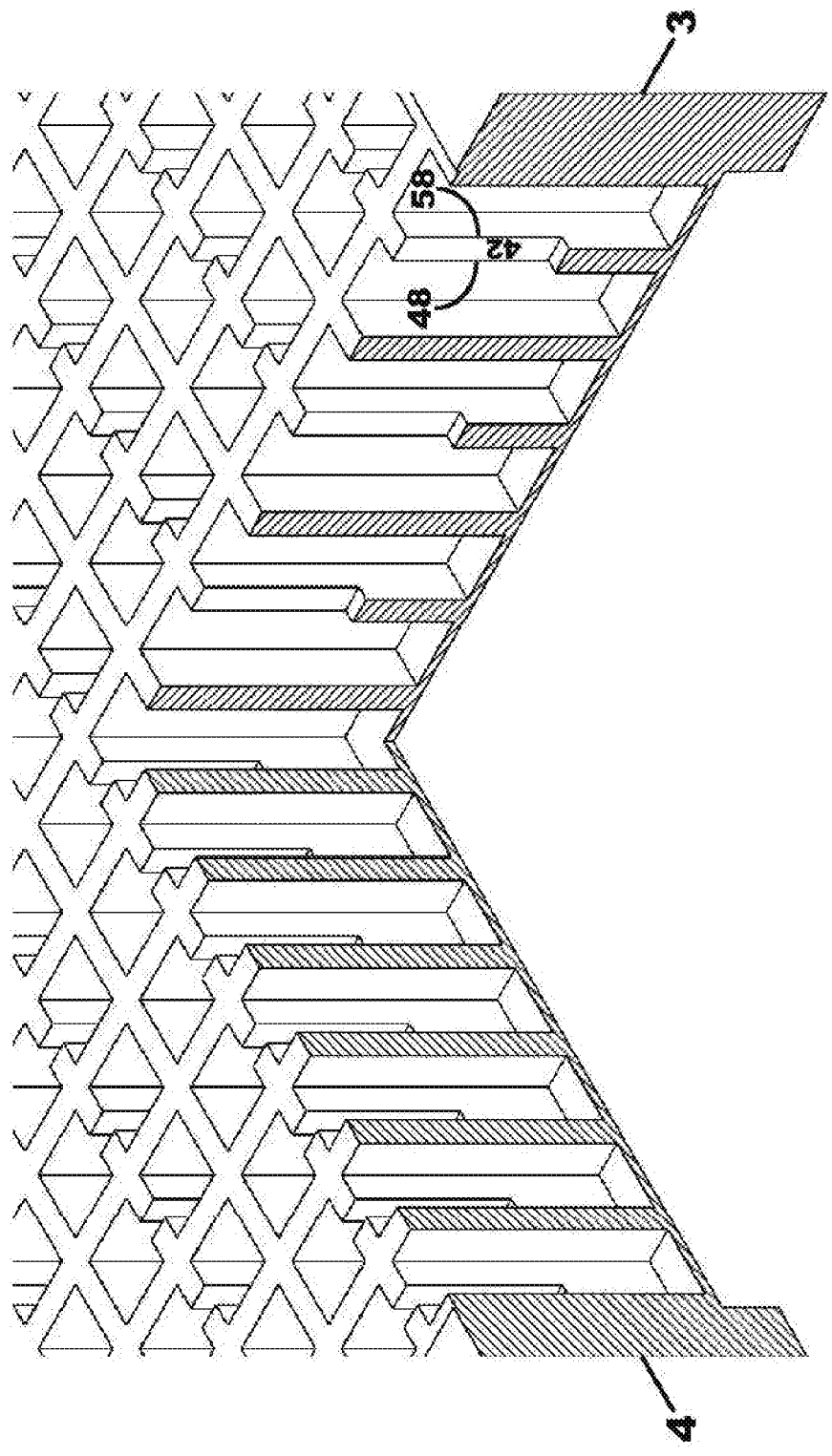
FIG. 2B is an isometric view thereof.
Figures 8, 8A:
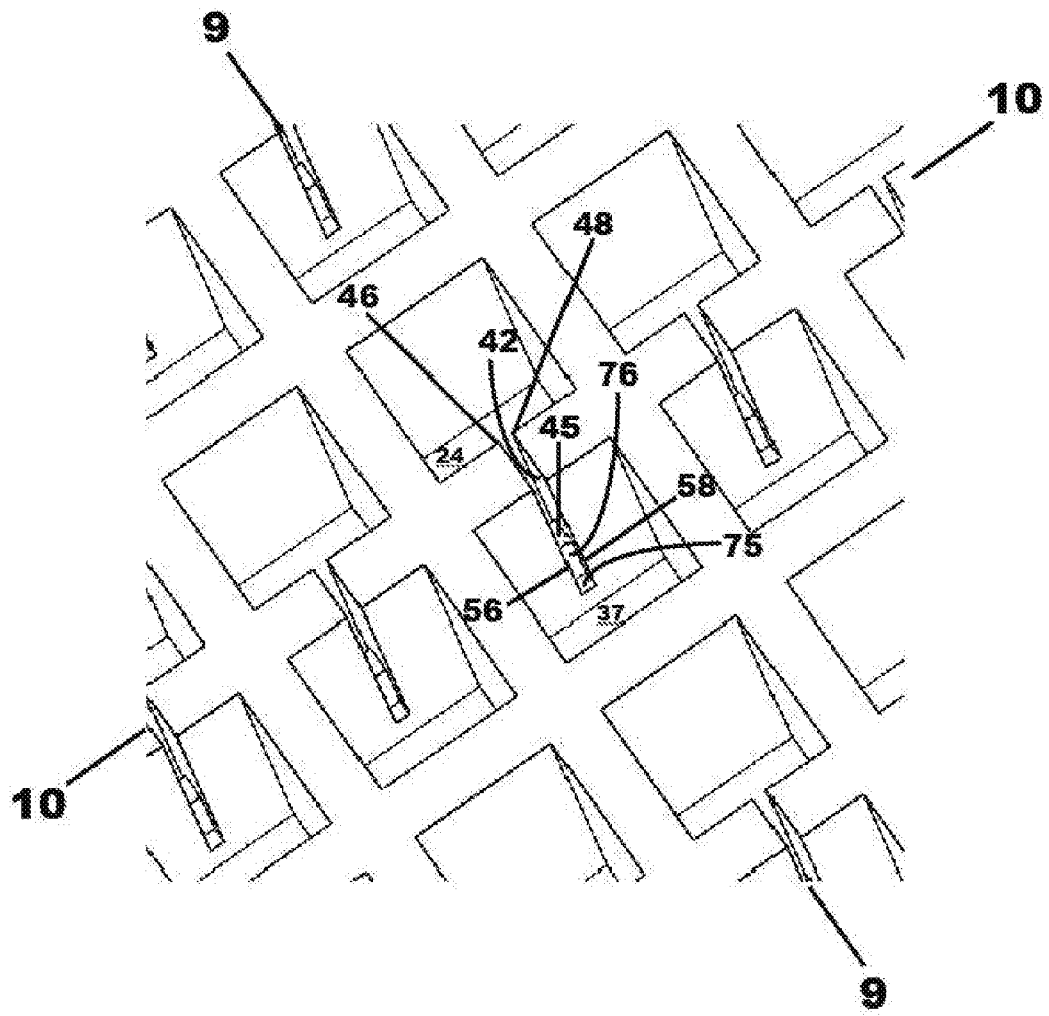
FIG. 8.
FIG. 8A and FIG. 8B are isometric views of an alternate embodiment of a device of embodiments of the present disclosure; capillary channel.
Figures 8, 8B:
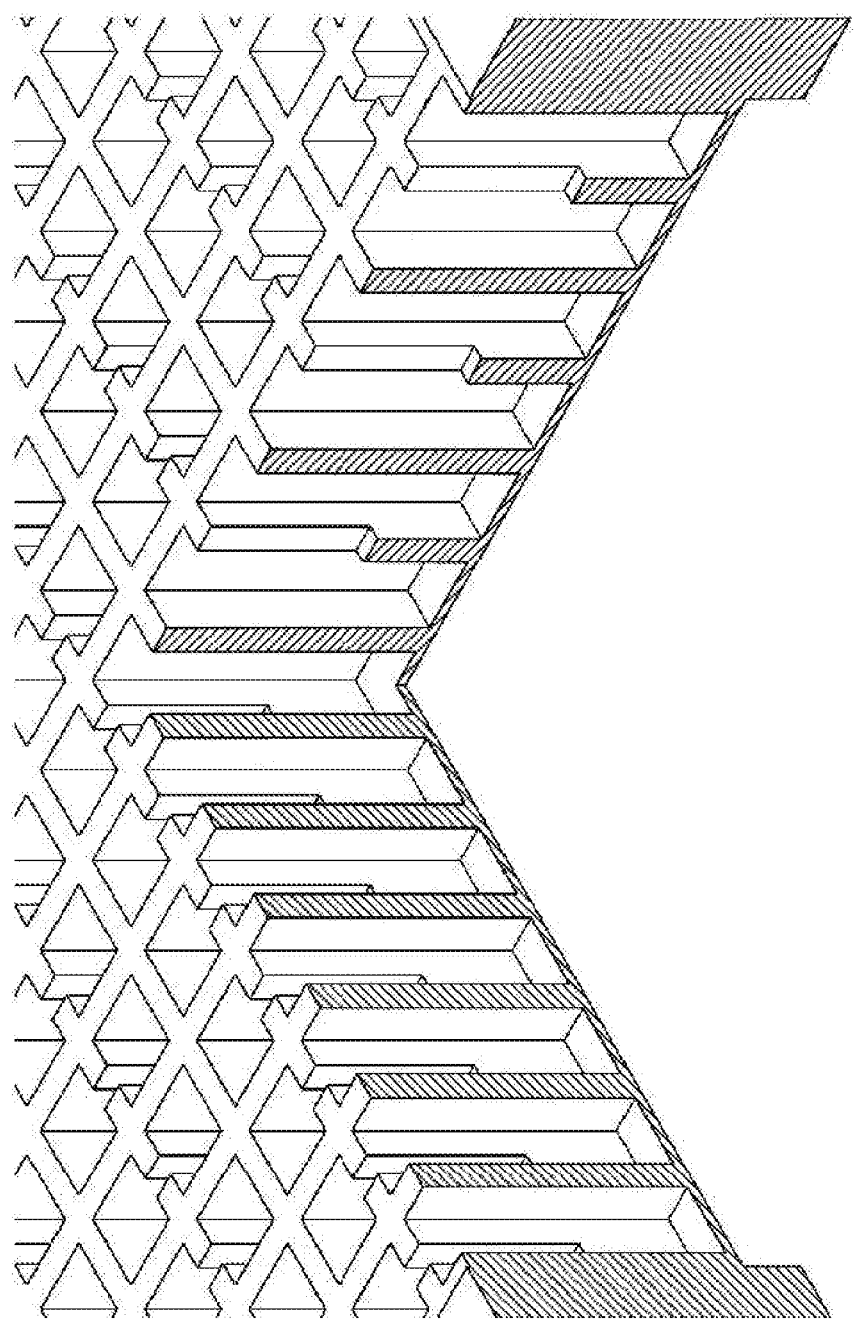
Figure 9:
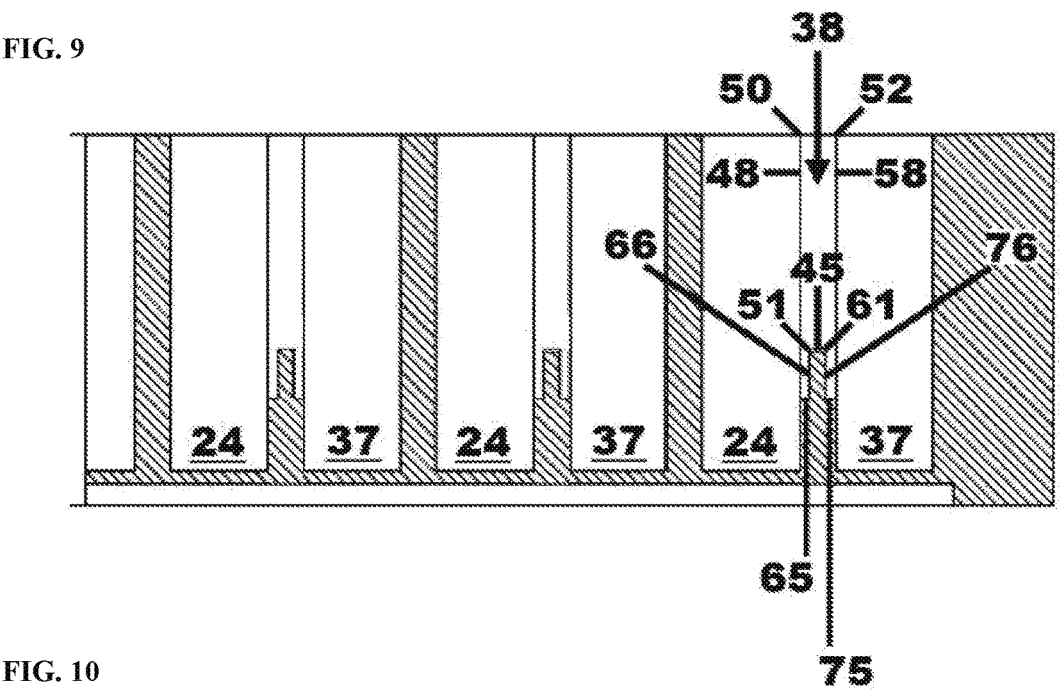
FIG. 9 is a schematic, cross-sectional view of adevice of embodiments of the present disclosure taken along line 9-9 of FIG. 8; cross section of capillary channel.
Figure 10:
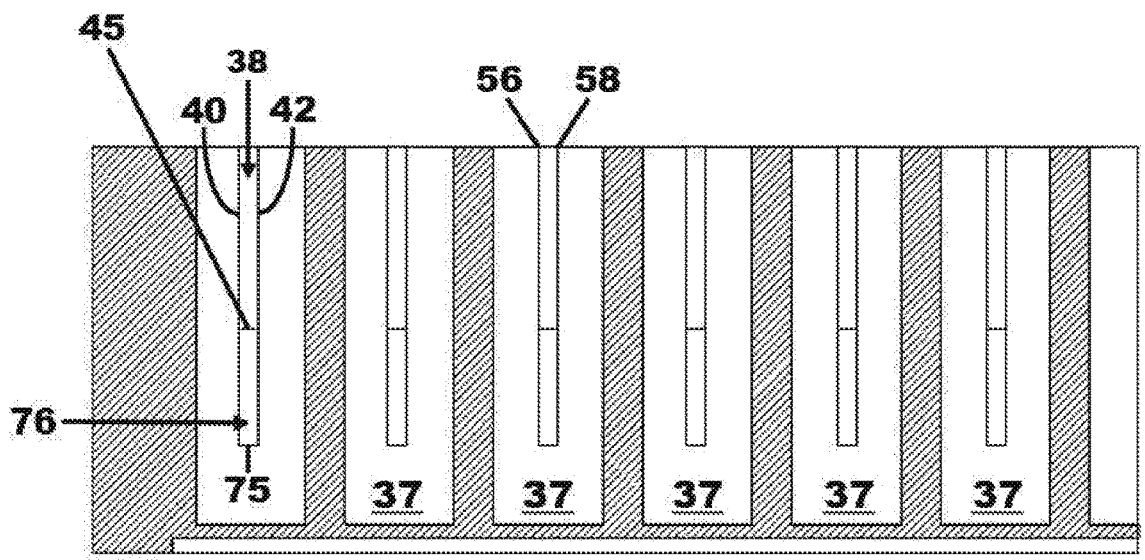
FIG. 10 is a schematic, cross-sectional view of the device taken along line 10-10 of FIG. 8.
Figure 11:
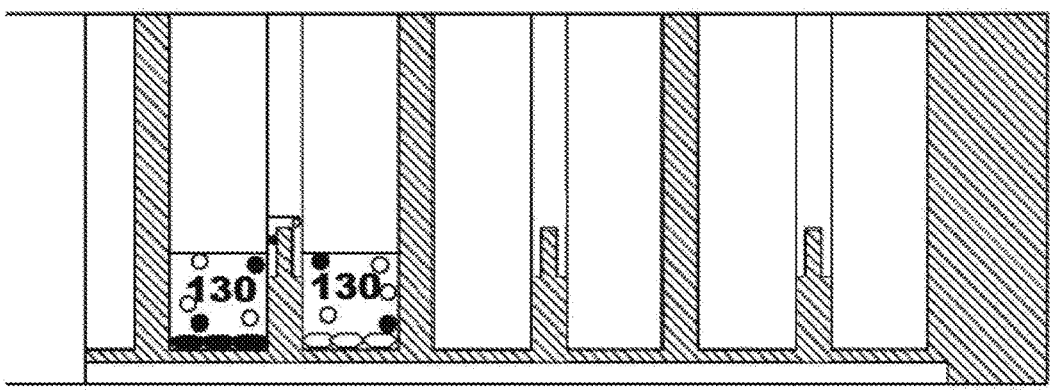
FIG. 11 is a schematic, cross-sectional view of adevice of embodiments of the present disclosure, similar to FIG. 9, showing a still further step of the methodology of embodiments of the present disclosure.

As used herein, the term "cell culture" or "culture" refers to the process by and conditions under which cells or tissue is maintained under artificial conditions for a short or long time outside of the organism from which it was originally extracted. "Cell culture" is a generic term that may also encompass the cultivation of prokaryotes and eukaryotes. The term "mono-culture" refers to a type of cell culture in which all cultured cells are the same type. Culturing, as used herein, can include, but does not require, cell division of cultured cells.

As used herein, the term "cellular co-culture" or "co-culture" refers to the process by which a mixture of two or more different cell types are grown together or the mixture itself. The term "trans-co-culture" refers to the process or system of growing together different cell types from different sources (e.g., patients). For example, "trans-co-culture" describes a system in which Patient A's cancer cells are cultivated with Patient B's stromal cells. The term "cis-co-culture" refers to the process or system of growing or maintaining together different cell types from the same source (e.g., patient). For example, "cis-co-culture" describes a system in which Patient A's cancer cells are cultivated with Patient A's stromal cells. For either type of co-culture, the different cell types can be harvested at different times and stored for different lengths of time. In some forms of "cis-co-culture", cells of one type are frozen or cultured for several days before cells of a different type are collected and the "cis-co-culture" is assembled.

As used herein, the term "cancer" refers to any hyperproliferative disease that includes a malignancy characterized by deregulated or uncontrolled cell growth. Cancers of virtually every tissue are known. Examples of cancers include, but are not limited to carcinoma, lymphoma, blastoma, sarcoma, and leukemia or lymphoid malignancies. The term "hematological cancer" or "hematological malignancy" refers to any malignancy associated with cells in the bloodstream, bone marrow, or lymphoid system. Hematological cancers include but are not limited to Hodgkin's lymphoma, non-Hodgkin's lymphoma, lymphoblastic leukemia (acute and chronic), or multiple myeloma. The term "multiple myeloma" refers to a disseminated malignant neoplasm of plasma cells which is characterized by multiple bone marrow tumor foci and widespread osteolytic lesions. The term "Hodgkin's lymphoma" refers to cancer originating from the lymphocytes and characterized by the orderly spread of disease from one lymph node group to another and by the development of systemic systems with advanced disease.

As used herein, the term "microfluidic" refers to a device or system through which materials, particularly fluid born materials such as liquids, are transported on a microscale, and in some embodiments on a nanoscale. "Microfluidic systems" are systems arranged to deliver small amounts of fluid, for example, less than 1 ml of fluid.

The term "agent", as used herein, includes a compound that induces a desired pharmacological and/or physiological effect. The term also encompass pharmaceutically acceptable and pharmacologically active ingredients of those compounds including but not limited to their salts, esters, amides, prodrugs, active metabolites and analogs. This term includes the active agent per se, as well as its pharmaceutically acceptable, pharmacologically active salts, esters, amides, prodrugs, metabolites and analogs. The term "agent" is not to be construed narrowly but extends to small molecules, proteinaceous molecules such as peptides, polypeptides and proteins as well as compositions comprising them, and genetic molecules, such as RNA, DNA and their mimetics and chemical analogs, as well as cellular agents. The term "agent" includes a cell which is capable of producing and secreting the polypeptides referred to herein as well as a polynucleotide comprising a nucleotide sequence that encodes this polypeptide. Thus, the term "agent" extends to nucleic acid constructs including vectors such as viral or non-viral vectors, expression vectors and plasmids for expression in and secretion in a range of cells.

As used herein, the term "drug" refers to any substance intended for use in the diagnosis, cure, mitigation, treatment, or prevention of disease, or to affect the structure or function of the body. The term "drug" refers to a variety of substances including but in no way limited to afatinib, denosumab, lenalidomide, trametinib, dabrafenib, radium Ra 223 dichloride, erlotinib, ado-trastuzumab emtansine, acetylsalicylic acid, bergamottin, dihydroxybergamottin, paradicin-A, pomalidomide, doxorubicin hydrocholoride, bevacizumab, bortezomib, docetaxel, aziridines, streptozotocin, cytarabine, podophyllotoxin, actinomycin, cyclophosphamide, methotrexate, 5-fluorouracil, vinblastine, dacarbazine, and prednisolone.

As used herein, the term "patient" refers to animals, including mammals, preferably humans.

As used herein, the term "in vivo" means within a living organism and "ex vivo" means outside of a living organism.

As used herein, the term "in vitro" refers to operations carried out in an artificial system.

As used herein, the term "fluid connection" or "fluidically connected" or similar means that a system allows fluid to flow between two or more elements. Two reservoirs can be physically isolated by a barrier but fluidically connected by channels that allow fluid to flow between them or agents to diffuse within that fluid connection with or without fluid flow.

As used herein, the term "channel" or "diffusion pore" refers to pathway in or through a medium that allows for movement of fluids such as liquids or gases, which may contain soluble factors. In some embodiments, "channels" of devices of embodiments of the present disclosure are between 3.5 mm and 1.0 µm in width. The term "microchannel" refers to a channel having cross-sectional dimensions in the range of about 1.0 µm to 500 µm, preferably between about 15 µm and 200 µm. As used herein, the term "chamber" or "well" refers to any structure in which volumes of fluid can be contained.

DETAILED DESCRIPTION

Provided herein are microtiter plates, systems, and uses thereof. In particular, provided herein are microtiter plates with diffusion channels and their use in co-culture applications (e.g. in high throughput screening).

For example, in some embodiments, the present disclosure provides a microtiter plate based device, system and method for use in screening assays (e.g., high throughput screening (HTS) assays). In some embodiments, the devices, systems, and methods described herein find use in drug development and toxicity screening. In some embodiments, to address challenges with existing devices, computerized numerical control (CNC) micro-milling or injection molding or any other suitable manufacturing process is used to engineer microtiter plates with micro-scale diffusion channels between adjacent wells of a HTS microtiter plate. This modification adds co-culture capability to microtiter plate formats. This device and method allows for cellular cross-talk through diffusion of small molecules between reaction wells. It also enables metabolic competence in high throughput screening assays by allowing diffusion of metabolites generated in one well to diffuse to an adjacent well.

In some embodiments, to implement an assay, cells are monocultured in individual wells as usual, but by increasing fluid volume, the media from monocultures in adjacent wells are bridged through the integrated microchannels allowing co-culture through diffusion of metabolites between wells. Controlling well volume and the geometry of the microchannels that bridge these compartments enables predictable and controlled diffusion, capillary flow or gravity driven flow rates between multiple (e.g., 2 to 8) adjacent wells in a format that is amenable to HTS. This allows secreted metabolites from one cell type (e.g., primary cells, immortalized cells, cancer cells, pluripotent cells (e.g., stem cells), etc.) in a "bioactivator" well to diffuse into adjacent "reporter" wells containing, e.g., a second (e.g., reporter) cell type or assay reagent (e.g., for a reporter gene assay, a biochemical assay, a drug screening assay, a toxicity assay, etc.). In some embodiments, the cells cultured in the bioactivator well are pre-incubated or co-incubated with a test compound to provide a bolus or continuous source of metabolized compounds for the duration of the reporter assay. The present disclosure provides a solution to an increasingly challenging problem with a minimal added footprint compared to standard HTS assays.

There are many other applications for utilizing high-throughput co-culture assays. Interactions between different cells types are integral to cell biology. For example, cellular cross talk can drive differentiation of stem cells or confer invasive characteristics to cancer cells. To date, it has been difficult to study these interactions in vitro. For one reason, adding additional cell types exponentially increase the number of parameters to optimize to identify viable conditions for these cultures in vitro.

FIGS. 1-11 illustrate a device for conducting separate biological cultures, biological or chemical reactions and then connecting reactions through channels allowing co-culturing and transport of small molecules, such as metabolites, produced in a compartment and transported by a process such as diffusion, capillary flow or gravity driven flow into an adjacent well with another cell type or biological assay. Device 10 includes first and second ends 13 and 15, respectively; first and second sides 17 and 19, respectively; and upper and lower surfaces 21 and 23, respectively. Device 10 is made up of an array of sets of at least 2 or more compartments 12 and 26 connected by a channel 38 for the transfer of small molecules from one compartment to the other(s). Other configurations are possible without deviating from the scope of the present disclosure.

Device 10 further includes a source compartment or well 12 defined by first and second sidewalls 14 and 16, respectively, first and second end walls 11 and 20, respectively, and bottom wall 22. Source well 12 includes input 25 communicating with upper surface 21 of device 10. Upper edges of side walls 14 and 16 are generally parallel to each other and generally perpendicular to the upper edges of first and second endwalls 11 and 20, respectively. Lower edges 14 and 16 of sidewalls intersect corresponding lower edges of first and second end walls 11 and 20, respectively. In the depicted embodiment, input 25 has a generally squared configuration, but it can be appreciated that other configurations such as round are possible without deviating from the scope of the present disclosure.

Bottom wall 22 of a well 12 lies in a first plane, for reasons hereinafter described. Inner surfaces 14a and 16a of sidewalls 14 and 16, respectively, inner surfaces 18a and 20a of first and second end walls 18 and 20, respectively, and upper surface 22a of bottom wall 22 define source cavity 24. While input well 12 has a generally rectangular configuration in the depicted embodiment, other configurations are contemplated without deviating from the scope of the present disclosure. It can be appreciated that a user can fill source cavity 24 with a fluid, cells or a biochemical reaction components through input 25 of input well 12.

Second well 26 is provided in device 10 adjacent to source well 12. Second well 26 is defined by first and second sidewalls 28 and 30, respectively, upstream wall 32, down stream wall 34 and bottom wall 36 plane. Inner surfaces 28a and 30a of sidewalls 28 and 30, respectively, inner surface 32a of upstream wall 32, inner surface 34a of downstream wall 34, and upper surface 36a of bottom wall 36 define second cavity 37 for small molecules, e.g. metabolites to difuse as hereinafter similar to FIG. 7, showing a third step of the methodology of scope of the present disclosure.

Input well 12 and second well 26 are interconnected by first passage 38. First channel 38 extends along an axis 39 which is vertically spaced from and above the first and second planes. First channel 38 is defined by first and second side walls 40 and 42, respectively, and bottom wall 45. Input ends 46 and 48 of first and second sidewalls 40 and 42, respectively, of first channel 38 and input ends 50 and 51 of upper and bottom walls 44 and 45, respectively, of input channel 38 intersect end wall 20 of input well 12 so as to define input 52 to first channel 38. Output ends 56 and 58 of first and second sidewalls 40 and 42, respectively, of first channel 38 and output end 61 of bottom 45, of first channel 38 intersect upstream wall 32 of second well 26 so as to define output 62 of first channel 38. First and second sidewalls 40 and 42, respectively, of first channel 38 are generally parallel to each other.

FIGS. 5-7. In operation, it is intended to utilize device 10 and compartment 12 to house fluid 106 which is compatible with cell growth or reaction progression allowing for small molecules, such as metabolites, signaling molecules, and/or proteins, added to or released into fluid 106 creating a fluid 110 located in compartment 12. Once mixed with biological fluid 106, small molecules, added factors and fluid 106 becomes, fluid 110.

Likewise, it is intended to utilize device 10 and compartment 26 to house fluid 116 which is compatible with cell growth or reaction progression allowing for small molecules, such as metabolites, signaling molecules, and/or proteins, released into fluid 116 creating a conditioned fluid 120 which is inundated with small molecules produced from cells or reactions located in compartment 26. Once mixed with biological fluid 116, small molecules and fluid 106 becomes fluid 120.

In some embodiments, additional fluid is added initially or after a period of time, to cavity 24 increasing the fluid level 106 or 110 to a height which allows it to enter channel 38 and join with fluid 116 or fluid 120. Over time, fluids 106 or 110 and 116 and 120 fully mix forming fluid 130. A volume of fluid 130 may later be removed re-isolating the fluid compartments.

FIGS. 8-11 In some embodiments, the ends of channel 38 contain a capillary channel (<1000 um wide) inset within, but not through wall 20 and/or 32 that extends down from wall 45 creating walls 65 or 75 parallel to wall 45 and walls 66 and 76 perpendicular to wall 45. As above, in this iteration channel 38 is defined by first and second side walls 40 and 42, respectively. Bottom walls 45, 65, and 75, as well as inner walls 66 and 76. Input ends 46 and 48 of first and second sidewalls 40 and 42, respectively, of channel 38 and input ends 50 and 51 of bottom walls 45, 65, and 75, of input channel 38 intersect end wall 20 of input well 12 so as to define input 52 to first channel 38. Output ends 56 and 58 of first and second sidewalls 40 and 42, respectively, of first channel 38 and output end 61 of bottom 45, of first channel 38 intersect upstream wall 32 of second well 26 so as to define output 62 of first channel 38. First and second sidewalls 40 and 42, respectively, of first channel 38 are generally parallel to each other. The inset capillary channel allows flow of fluid 110 to fluid 120 creating fluid 130 as above through capillary action with or without additional filling.

As described, the methodology of the present disclosure does not require any electronic equipment such as centrifuges, rockers/shakers, fluid pumps, while consuming only minimal volumes of reagents in the compartments, although the device is compatible with such equipment.

Figure 12:
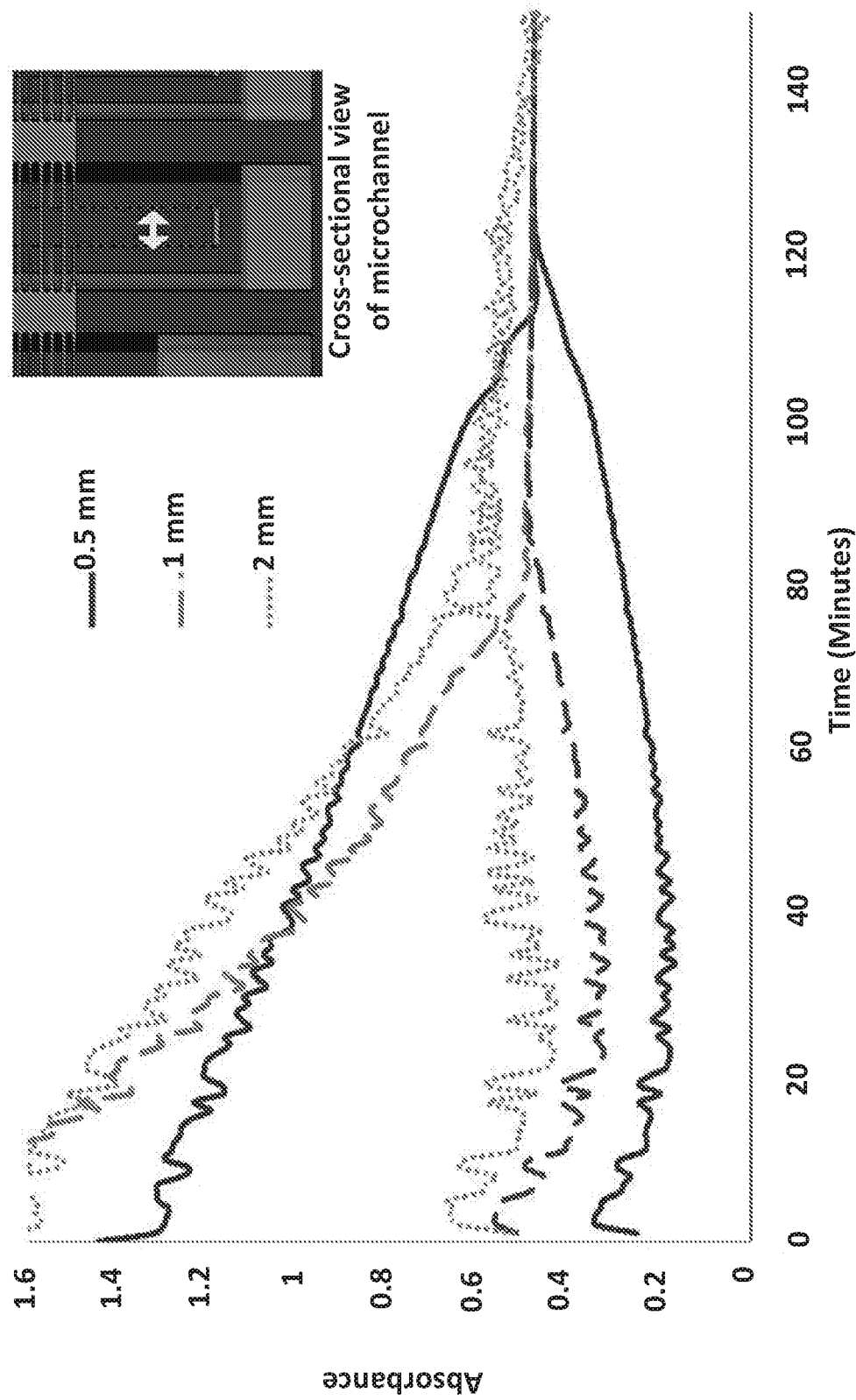
FIG. 12 shows that microchannel geometry controls rate of diffusion. Change in absorbance of bioactivator (dashed line) and reporter well (solid lines) is shown over time after adding 1 microliter of concentrated dye in the bioactivator well.
Figure 13:
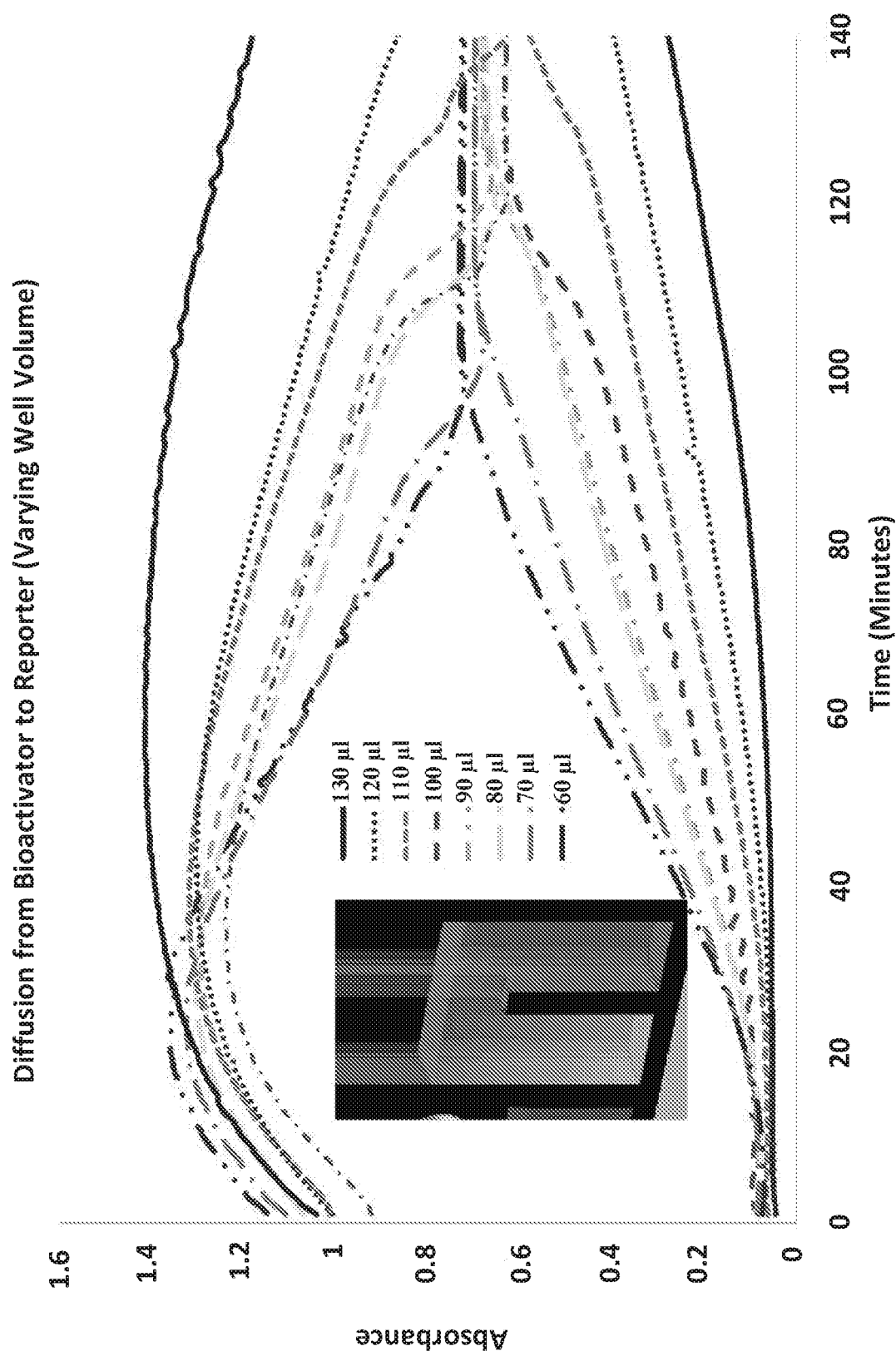
FIG. 13 shows that volume level controls rate of diffusion. Change in absorbance of bioactivator (dashed line) and reporter well (solid lines) is shown over time after adding 1 microliter of concentrated dye in the bioactivator well.
Figure 14:
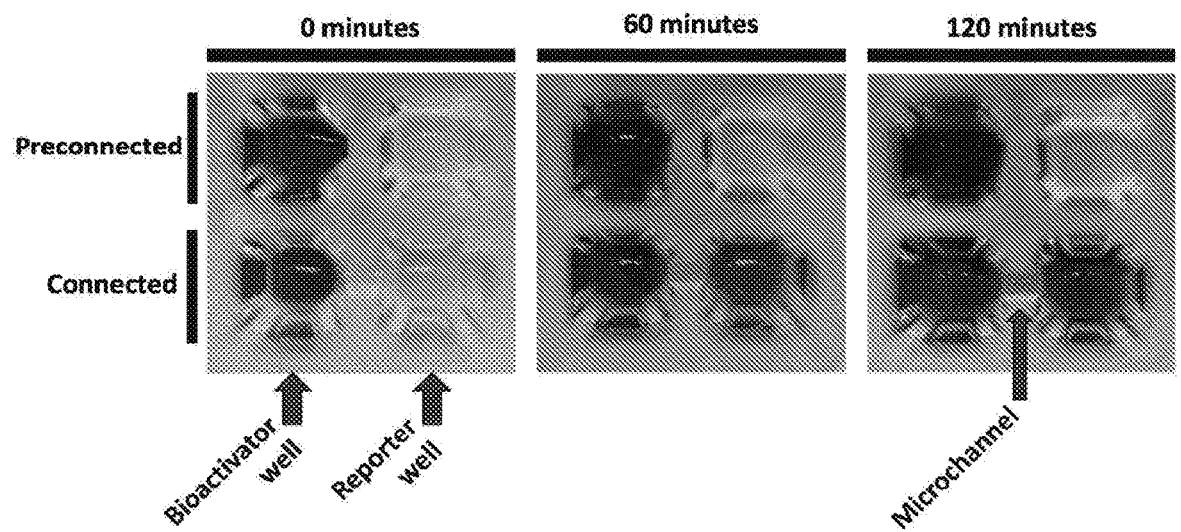
FIG. 14 shows diffusion of dye in preconnected and connected wells. Diffusion occurs only after wells are connected and reaches equilibrium in two hours.
Figure 15:
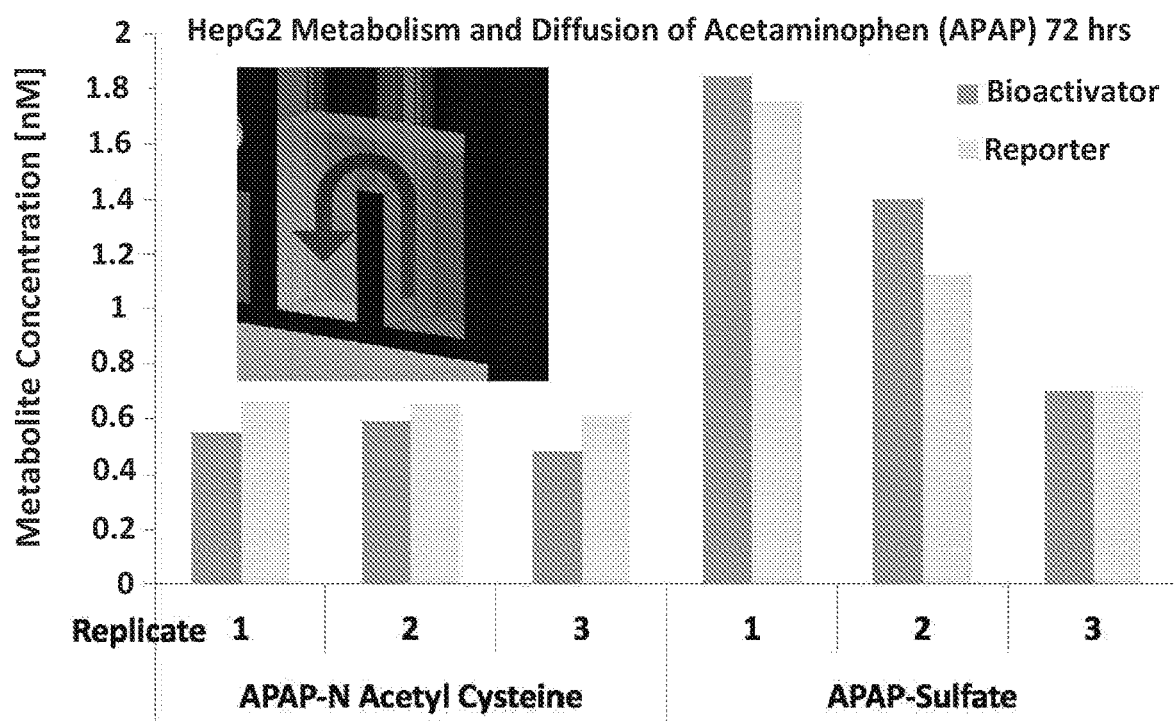
FIG. 15 shows that metabolites generated in the bioactivator well diffuse into reporter wells through the microchannel.
Figure 16:
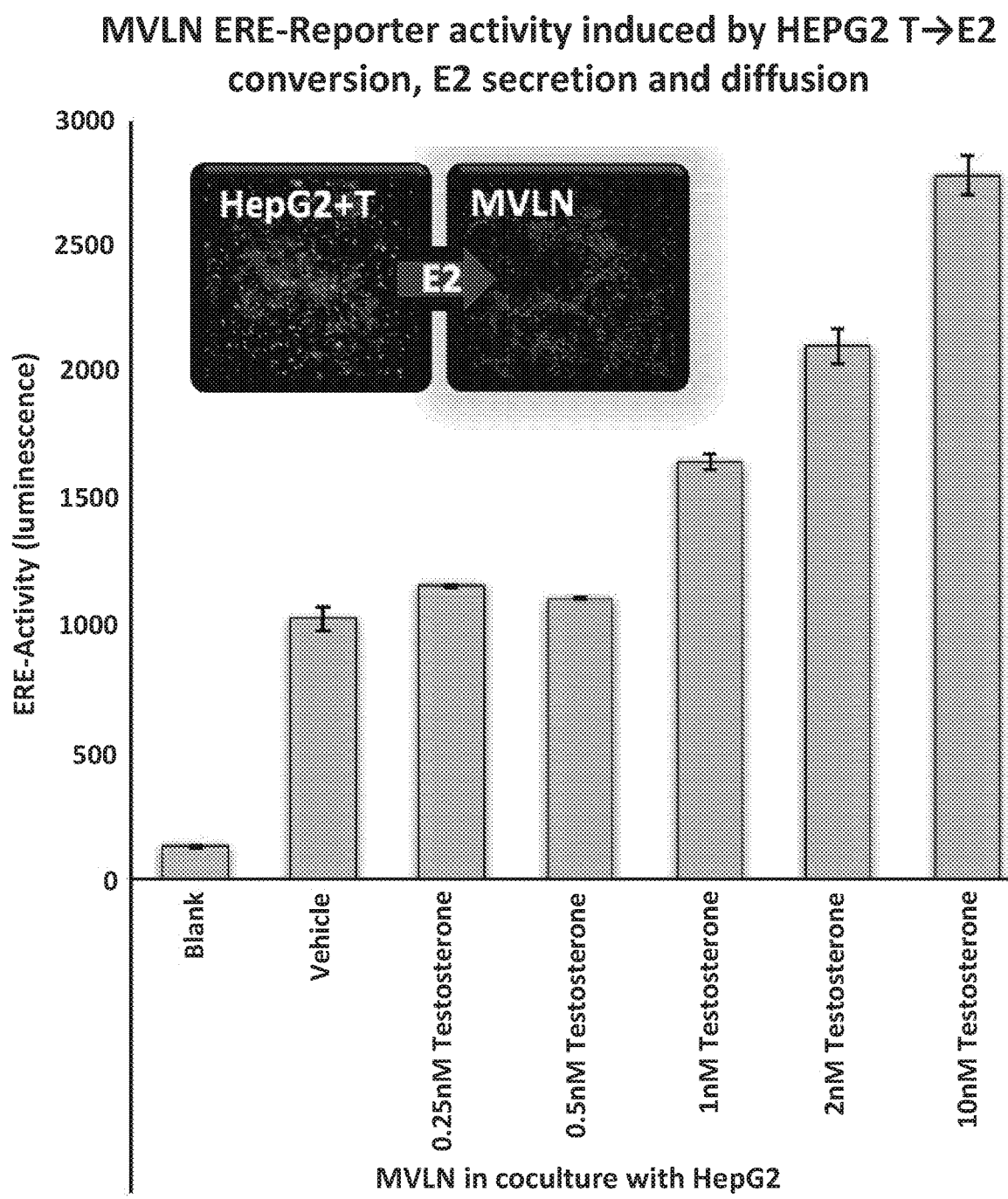
FIG. 16 shows that HepG2-dependent testosterone metabolism to estradiol activates MVLN reporter activity.

FIGS. 12-18 show exemplary devices in use. FIGS. 12 and 13 show that microchannel geometry and volume of media controls the rate of diffusion. To perform these assays, one microliter of a concentrated aqueous solution of crystal violet was pipetted to the bottom of the well (upper curves) and allowed to diffuse over time into an adjacent well (lower curves), curves from connected wells are shown in the same line pattern. The decrease in absorbance in the bioactivator well and the increase in absorbance in the reporter well were monitored on a (Molecular Devices) Spectramax (Molecular Devices) 384 well plate reader. The time to equilibrium is shown to vary based on both the fluid volume in the well and the width of the microchannel. FIG. 14 shows diffusion of dye through channels as in FIGS. 12 and 13, which occurs only after the fluid in connected in the microchannel. FIG. 15 demonstrates diffusion of metabolites through channels. Acetaminophen (10 uM) was incubated with HepG2 cells for 72 hours in the bioactivator well, no cells were cultured in the adjacent reporter well, but media in each well was connected through the microchannel. Acetaminophen metabolites were quantified by HPLC with a diode array detector at 254 nm, and identified by matching retention time of known standards. The data shows that metabolites excreted by cells in the bioactivator well in standard culture conditions are able to diffuse to the adjacent well and maintain equilibrium. FIG. 16 shows that the device and method work in a HTS assay. MVLN cells cultured alone do not express the enzyme Cyp19 (aromatase) and therefore cannot convert testosterone into estrogen which induces a estrogen receptor driven luciferase reporter protein stably expressed in the MVLN cell line. Co-culture of HepG2 cells in one embodiment of the device with MVLN cells enables the conversion of testosterone into estrogen by HepG2 cells which express Cyp19, estrogen is released into the media where it diffuses into the adjacent well and induces the estrogen receptor driven luciferase reporter protein stably expressed in the MVLN cell line.

Figure 18:
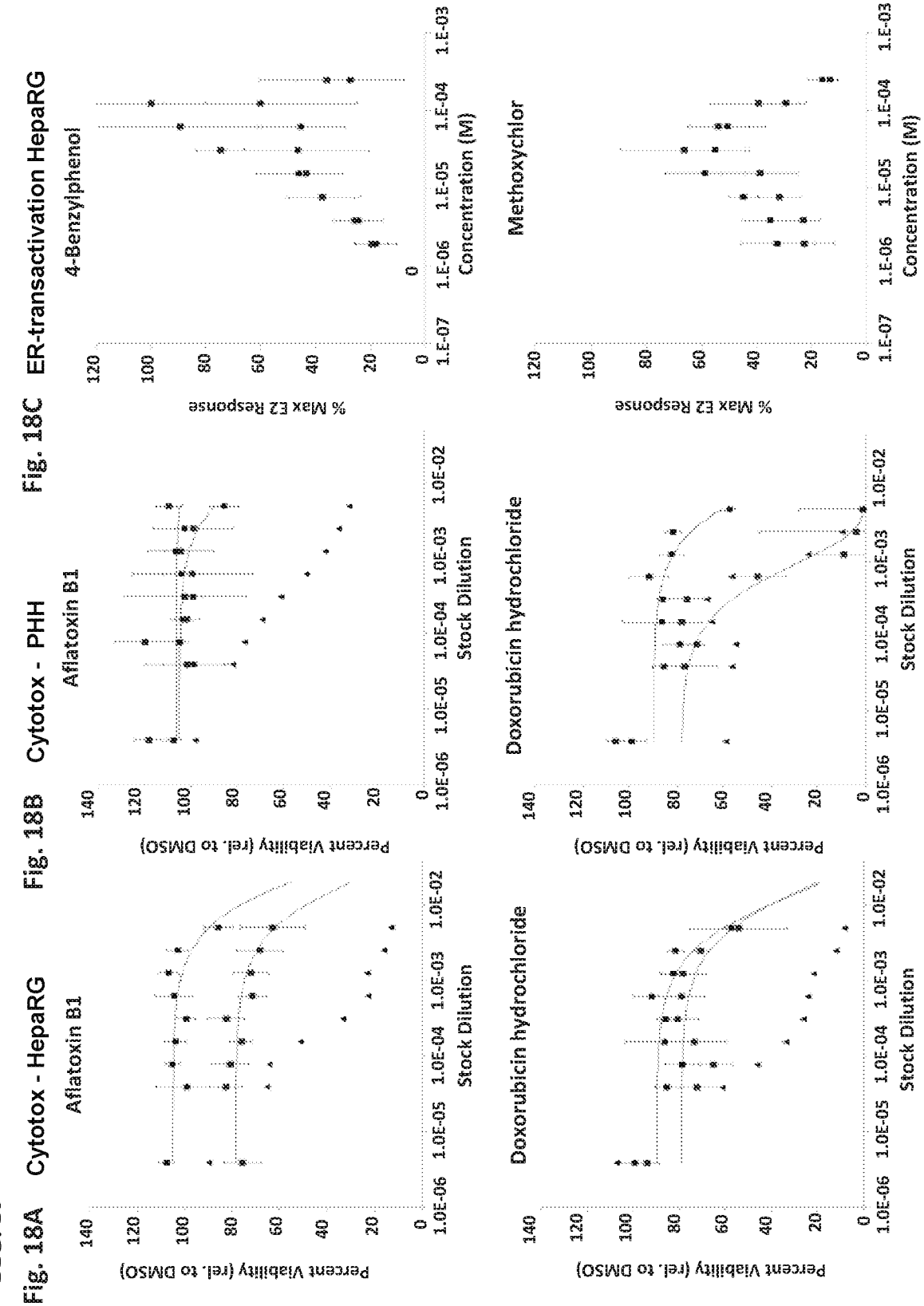
FIG. 18 shows that exemplary devices described herein provide metabolic competence.

FIG. 18 shows that major HTS readouts are supported by devices described herein. Absorbance and luminescent assays were performed to test the performance of an exemplary device. A conferred cytotoxicity assay was performed using HEK293 cells alone or in co-culture with HepaRG cells or primary human hepatocytes in the device. It was found that HepaRG cells and PHH differentially conferred toxicity of aflatoxin and doxorubicin, respectively (FIGS. 18a,b). MVLN luciferase cells were co-cultured with HepaRG cells in the reporter well. Results show that HepaRG metabolism induced increased MVLN luminescence relative to mono-culture (FIG. 18c). These studies show that the device finds use in a technically simple format that is amenable to HTS.

Because the device can utilize immortalized or primary human hepatocytes, it is able to provide chemical metabolism information relevant to toxicological effects. The bioactivator well is suitable for use in the culture of any primary cell or cell line as a source for chemical metabolism. In some embodiments, bioactivator cells are engineered to under-express/over-express phase I, phase II, or phase III enzymes/transporters to improve chemical metabolism and secretion of metabolites. The most common enzymes, Cytochrome P450 (1A1, 1A2, 2A6, 2B6, 2C8, 2C9, 2C19, 2D6, 2E1, and 3A4) and UGT, SULT that metabolize chemicals, are expressed in the immortalized HepaRG line used in FIG. 18 as well as primary human hepatocytes.

Together, these results show that the device and method are able to confer metabolic competence to HTS assays. The microchannel geometry can be controlled to enable different diffusion rates, allow capillary or gravity flow between 2 or up to 8 wells. Different metabolites produced by one cell type are able to diffuse into the adjacent well under standard culture conditions. In addition, a complete co-culture experiment where co-culture of two different cell types together are able to complete a reaction that neither can do on their own was demonstrated.

The present disclosure is not limited to particular applications. Examples include, but are not limited to, metabolic assays, screening of compounds (e.g., on cell growth, toxicity or metabolism), differentiation of pluripotent cells (e.g., by enabling paracrine signaling agents to be secreted by other cell types driving differentiation), etc.

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in the relevant fields are intended to be within the scope of the following claims.

We claim:

1. A cell culture device, comprising:
    i) a plurality of first wells having a sidewall, an end wall, and a bottom wall, wherein a distance from said bottom wall of said first wells and an upper edge of said sidewall of said first wells defining a depth of said first wells;
    ii) a plurality of second wells, said plurality of second wells having a side wall, an end wall, and a bottom wall, wherein a distance from said bottom wall of said second wells and an upper edge of said sidewall of said second wells defining a depth of said second wells;
    wherein said second wells are adjacent with said first wells such that said end wall of said first wells is said end wall of said second wells;
    wherein said end wall connects with said bottom walls of said first and second wells to form a physical and fluidic barrier between said first and second wells;
    wherein at least a portion of said end wall has a height less than said first and second depths, such that fluid in either first or second wells flows over said end wall when said fluid has a level exceeding said height and wherein fluid is prevented from moving between said first and second wells when said fluid has a level less than said height.

2. The device of claim 1, wherein said device is a microtiter plate.

3. The device of claim 2, wherein said microtiter plate comprises 6, 24, 96, 384 or 1536 wells.

4. The device of claim 1, wherein at least a portion of said end wall that has a height less than said first and second depths forms a channel between said first well and said second well.

5. The device of claim 4, wherein said channel is filled with a membrane.

6. The device of claim 5, wherein said membrane is selected from the group consisting of a gel, a hydrogel, and a porous membrane.

7. The device of claim 5, wherein said membrane excludes molecules of a specific size or diffusion rate from passing through said channel.

8. A system, comprising:
    a) the device of claim 1; and
    b) a plurality of cells in one or more of said first or second wells.

9. The system of claim 8, wherein said system further comprises one or more additional components selected from the group consisting of a fluid, a fluid transport component, a plurality of second cells of a different cell type, a test compound, and components for performing a biological assay.

10. The system of claim 8, wherein said plurality of cells are selected from the group consisting of primary cells, immortalized cells, microbial cells, and stem cells.

11. The system of claim 8, wherein said second cells are reporter cells.

12. The system of claim 8, wherein said fluid is buffer or culture media.

13. The system of claim 8, wherein said biological assay is selected from the group consisting of a gene expression assay, a cell signaling assay, a toxicity assay, and a drug screening assay.

14. The device of claim 1, wherein said device comprises sets of first wells and second wells.

15. The device of claim 14, wherein said sets comprise two or more first wells and two or more second wells.

16. The device of claim 15, wherein said sets comprise one first well and one second well.

* * * * *